US005576351A

United States Patent [19]
Yoshimura et al.

[11] Patent Number: 5,576,351
[45] Date of Patent: Nov. 19, 1996

[54] USE OF ARGININE AS AN IMMUNOSTIMULATOR

[75] Inventors: Norman N. Yoshimura, Westminster, Calif.; Adrian Barbul, Baltimore, Md.; Robert C. Tao, Huntington Beach, Calif.; Michael C. Storm, Laguna Niguel, Calif.; Robert E. Kelley, Orange, Calif.; Brenda L. Reis, Costa Mesa, Calif.

[73] Assignee: McGaw, Inc., Irvine, Calif.

[21] Appl. No.: 341,443

[22] Filed: Nov. 16, 1994

Related U.S. Application Data

[63] Continuation of Ser. No. 964,567, Oct. 21, 1992, abandoned, which is a continuation of Ser. No. 635,746, Dec. 28, 1990, abandoned, which is a continuation-in-part of Ser. No. 458,996, Dec. 29, 1989, abandoned.

[51] Int. Cl.$^6$ .......................... A61K 31/195; A61K 31/19
[52] U.S. Cl. ........................... 514/565; 514/573; 514/885
[58] Field of Search .................................. 514/565, 573, 514/885

[56] References Cited

U.S. PATENT DOCUMENTS

| | | | |
|---|---|---|---|
| 3,950,529 | 4/1976 | Fischer et al. | 424/273 |
| 4,340,592 | 7/1982 | Adibi | 424/177 |
| 4,385,068 | 5/1983 | Kendall et al. | 424/319 |
| 4,439,448 | 3/1984 | Munakata et al. | 424/319 |
| 4,491,589 | 1/1985 | Dell et al. | 424/274 |
| 4,752,618 | 6/1988 | Mascioli et al. | 514/549 |
| 4,758,553 | 7/1988 | Ogoshi | 514/47 |
| 4,832,465 | 5/1989 | Ghadimi | 424/319 |
| 5,053,387 | 10/1991 | Alexander | 514/2 |
| 5,231,085 | 4/1993 | Alexander et al. | 514/44 |

FOREIGN PATENT DOCUMENTS

| | | |
|---|---|---|
| 0184999 | 11/1985 | European Pat. Off. . |
| 0367724 | 10/2789 | European Pat. Off. . |
| 3603242 | 6/1987 | Germany . |

OTHER PUBLICATIONS

Barbul, "Arginine: Biochemistry, Physiology, and Therapeutic Implications," JPEN, 10, 227–238 (1986).
Madden et al, "Prolonged Thymotropic Effect After One Week of Oral Arginine (ARG) Supplementation," Abstract. Fed. Proc., 46, 558, #1586 (1987).
Levenson et al, "Citrulline Replaces Arginine as a Dietary Essential in Rats; Ornithine Does Not," Fed. Proc. 39, 726, #2421 (1980).
Critselis et al, "Arginine Inhibits a Viral Tumor," Fed. Proc., 36, 1099, Abstract #4380 (1977).
Barbul et al, "Thymotropic Actions of Arginine (ARG), Ornithine (ORN) and Growth Hormone (GH)" Fed. Proc., 37, 264, Abstract #282 (1978).
Rettura et al, "Ornithine Inhibits Two Murine Tumors," Fed. Proc., 37, 358, Abstract #779 (1978).
Barbul et al, "Thymus–Arginine Interactions in Wound Healing (WH)," JPEN, 5, 567, Abstract #56 (1981).

Madden et al, "Prolonged Thymotropic Effect After One Week of Oral Arginine (ARG) Supplementation," (FASEB Abstract Form) (1987).
Barbul et al, "Arginine Increases The Number of T Lymphocytes in Nude Mice," JPEN, 13, 7S, Abstract #14 (1989).
Rettura et al, "Supplemental Vitamin A (VA) or L–Arginine (AR) Inhibit Regrowth of Transplanted C3HBA Tumors," 18th Mid–Atlantic Regional Meeting of the American Chemical Society, Apr., 1984, Newark, New Jersey.
Seifter et al, "Anabolic Effects of L–Arginine and L–Ornithine," Biochem 23, 3382 (1984).
Rettura et al, "Putrescine (PU) Does Not Have Thymotropic Properties of Ornithine (ORN) and Arginine (ARG)," J.Am. Col.Nutr., 1, 423, (1982).
Rettura et al, "Citrulline Does Not Share the Thymotropic Properties of Arginine and Ornithine," Fed. Proc, 38, 289, #343, 1980.
Seifter, "Supplemental Arginine Increases Survival in Mice Undergoing Local Tumor Excision," JPEN, 4, 589, Abstract #38 (1980).
Barbul et al, "Thymotropic Actions of Arginine (ARG) and Metabolites," J.Am.Col.Nut., 1, 115, Abstract #44 (1982).
Rettura et al, "Supplemental Arginine (ARG) and Ornithine (ORN) Promote Allograft Rejection," AGFD, Abstract #11 (1982).
Madden et al, "Stimulation of T Cell Immunity by Arginine Enhances Survival in Peritonitis," J.Surg.Res., 44, 658–663 (1988).
Barbul et al, "Optimal Levels of Arginine in Maintenance Intravenous Hyperalimentation," JPEN, 8, 281–284 (1984).
Barbul et al, "High Arginine Levels in Intravenous Hyperalimentation Abrogate Post–traumatic Immune Suppression," J.Surg.Res., 36, 620–624 (1984).
Barbul et al, "Wound healing and Thymotropic Effects of Arginine: A Pituitary Mechanism of Action," A.J.Clin.Nutr., 37, 786–794 (1983).
Barbul et al, "Nitrogen–Sparing and Immune Mechanisms of Arginine: Differential Dose–Dependent Responses During Postinjury Intravenous Hyperalimentation," Curr.Surg., 40, 114–116 (1983).

(List continued on next page.)

Primary Examiner—Marianne M. Cintins
Assistant Examiner—T. J. Criares
Attorney, Agent, or Firm—Christie, Parker & Hale

[57] ABSTRACT

The present invention relates to the treatment of an impaired human immune response or to reduction of the severity of degradation of the human immune response by the administration of arginine or ornithine, or a functional analog of arginine or ornithine, or mixtures thereof, to humans suffering from an impaired immune response or at risk of suffering an impaired immune response. Such treatment is provided by enterally administering compositions supplemented with arginine or ornithine, or functional analogs of arginine or ornithine, or parenterally administering amino acid solutions supplemented with arginine or ornithine, or functional analogs of arginine or ornithine, to the patient.

38 Claims, No Drawings

OTHER PUBLICATIONS

Barbul et al, "Immunostimulatory Action of Arginine in Humans," *Surg.Forum.*31, 82–84 (1980).

Barbul et al, "Thymic Stimulatory Actions of Arginine," *JPEN* 4, 446–449 (1980).

Barbul et al, "Arginie Stimulates Lymphocyte Immune Response in Healthy Human Beings," *Surg.*, 90, 244–251 (1981).

Barbul et al, "Arginine Stimulates Thymic Immune Function and Ameliorates the Obesity and the Hyperglycemia of Genectically Obese Mice," *JPEN*, 5, 492–495 (1981).

Barbul et al, "Metabolic and Immune Effects of Arginine in Postinjury Hyperalimentation," *Journal of Trauma*, 21, 970–974 (1981).

Seifter et al, "Arginine: An Essential Amino Acid for Injured Rats," *Surg.*, 84, 224–230 (1978).

Rettura et al, "Arginine Increases the Lymphocyte Content of Thymus Glands," *JPEN*, 1, Abstract #22A (1977).

Barbul et al, "Arginine (ARG) Improves Thymic Function in OB/OB Mice," *JPEN*, 4, 589, Abstract #37 (1980).

Barbul et al, "Optimal Levels of Arginine (ARG) in Maintenance IVH," *JPEN*, 6, 579 (1982).

Barbul et al, "Supplemental Arginine Wound Healing, and Thymus: Arginine–Pituitary Interaction," *Surg. Forum*, 24, 93–95 (1978).

Barbul et al., "Intravenous Hyperalimentation with High Arginine Levels Improves Wound Healing and Immune Function," *J.Surg.Res.*, 38, 328–334 (1985).

Barbul et al, "Immunostimulatory Effects of Arginine in Normal and Injured Rats," *J.Surg.,Res.*, 29, 228–235 (1980).

Susskind et al, "Regulatory Mechanisms in Cytotoxic T–Lymphocyte Development. II, Dissociation of In Vitro Cytotoxic T–lymphocyte and Suppressor T–Cell Activities with L–Ornithine," *Immunochem.*, 105, #151378s, #553 (1986).

Rettura et al, "Supplemental Arginine Increases Thymic Cellularity in Normal and Murine Sarcoma Virus–inoculated Mice and Increases the Resistance to Murine Sarcoma Virus Tumor," *JPEN*, 3, 409–416 (1979).

Barbul et al, "Thymic and Immune Stimulatory Actions of Arginine (ARG)," 4th Annual Meeting of the AmericanSociety for Parenteral and Enteral Nutrition, *JPEN*, 3, 500, #8 (1980).

Barbul et al, "Arginine: A thymotrophic and Wound–Healing Promoting Agent," *Surg. Forum* 28, 101–103 (1977).

Seifter et al, "Dietary Stimulation of T and B Lymphocyte Dependent Systems," 6th Annual Maine Biomed. Sci. Symp., Jun. 11–13, 1980.

Rettura et al, "Thymic and Wound Healing Actions of Arginine: Abolition by Hypophysectomy",: Am. Chem. Soc. 176th Mtg., Miami Beach, FL, Sep. 10–15, 1978.

Seifter et al, "Arginine (ARG) and Ornithine (ORN) Stimulate Allograft Rejection," Ajinomoto Symp., Amino Acids: Metabolism and Medical Application, Raleigh, NC, Mar. 31–Apr. 2, 1982.

Rettura et al, "Improved Wound Healing, Anti–Catabolic and Thymotropic Actions of Supplemental Ornithine (ORN)," 17th Middle Chem Div., White Haven, PA, Apr. 6–8, 1983.

Seifter et al, "Arginine: Thymotropic Effects," *Biol.*, Abstract #146, Am. Chem. Soc. 174th Mtg., Chicago, IL, Aug. 28–Sep. 2, 1977.

Barbul et al, "High IVH Arginine Levels Improve Wound Healing and Immune Function," Assn. Acad. Surg., San Antonio, TX, Oct. 30–Nov. 3, 1984.

Elsair et al, "Effect of Arginine Chlorhydrate on Nitrogen Balance During the Three Days Following Routine Surgery in Man," *Biomed.*, 29, 312–317 (1978).

Barbul et al, "Arginine and Wound Healing," *Fed. Proc.*, 36, 1099, Abstract #4380 (1977).

"Immun and Metabolic Effects of Arginine in the Surgical Patient," John M. Daly, et al, Department of Surgery, University of Pennsylvania School of Medicine, May 5, 1988.

Flyer entitled "IMPACT," prepared by Sandoz Company of Minneapolis, Minnesota (Sep. 1989).

Wagner et al, "Lipid–Based Parenteral Nutrition and the Immunosuppression of Protein Malnutrition," Arch Surg, vol. 119, Jul. 1984, pp. 809–810.

Neuvonen et al, "Lack of Modulation of Postoperative Immunosuppression by Isotonic Amino Acid Infusion," Journal of Parenteral and Enteral Nutrition, vol. 10, No. 2., pp. 160–165 (Mar.–Apr. 1986).

O'Mahony et al, "The Effect of Short Term Postoperative Intravenous Feeding Upon Cell–Mediated Immunity and Serum Suppressive Activity in Well Nourished Patients," Surgery, Gynecology & Obstetrics, vol. 159, pp. 27–32 (Jul. 1984).

Nuwer et al, "Does Modified Amino Acid Total Parenteral Nutrition Alter Immune–Response in High Level Surgical Stress," Journal of Parenteral and Enteral Nutrition, vol. 7, No. 6, pp. 521–524 (Nov.–Dec. 1983).

Blackburn et al., "Branched chain amino acid administration and metobolism during starvation, injury, and infection," *Surgery*, 86, 307–315 (1979).

Askanazi et al., "Muscle and Plasma Amino Acids after Injury: Hypocaloric Glucose vs. Amino Acid Infusion," *Ann. Surg.*, 191, 465–472 (1980).

Freund et al., "Infusion of the Branched Chain Amino Acids in Postoperative Patients: Anticatabolic Properties," *Ann. Surg.* 190, 18–23 (1979).

Freund et al., "Amino Acid Derangement in Patients with Sepsis: Treatment with Branched Chain Amino Acid Rich Infusions," *Ann. Surg.*, 188, 423–430 (1978).

Nachbauer et al., "Infusion of Branched Chain–Enriched Amino Acid Solutions in Sepsis," *Am. J. Surg.*, 147, 743–752 (1984).

Barbul et al., "Arginine enhances wound healing and lymphocyte immune responses in humans," *Surgery*, 108, 331–337 (19900.

Fox et al., "Effect of a Glutamine–Supplemented Enteral Diet on Methotrexate–Induced Enterocolitis," *JPEN*, 12, 325–331 (1988).

Souba et al., "Intestinal Consumption of Intravenously Administered Fuels," *JPEN*, 9, 18–22 (1985).

Burke et al., "Glutamine–Supplemented Total Parenteral Nutrition Improves Gut Immune Function," *Arch. Surg.*, 124, 1396–1399 (1989).

Ardawi et al., "Glutamine metabolism in lymphocytes of the rat," *Biochem. J.*, 212, 835–842 (1983).

Chyun et al., "Improvement of Nitrogen Retention by Arginine and Glycine Supplementation and Its Relation to Collagen Synthesis in Traumatized Mature and Aged Rats," *J. Nutr.*, 144, 1687–1704 (1984).

Patent Abstracts of Japan, vol. 9, No. 278 (c–312) (2001), 6th Nov. 1985; JP–A–60 123 413 (Ajinomoto K.K.) Feb. 7, 1985.

Patent Abstracts of Japan, vol. 11, No. 8 (c–396) (2455), 9th Jan. 1987; JP–A–61 186 320 (Morishita Seiyaku K.K.) Feb. 8, 1986.

Saito et al, "Metabolic and Immune Effects of Dietary Arginine Supplementation After Burn," Arch. Surg, vol. 122, No. 7, Jul. 1987, 784–789.

USE OF ARGININE AS AN IMMUNOSTIMULATOR

CROSS-REFERENCE TO RELATED APPLICATIONS

This is a continuation of application Ser. No. 07/964,567, filed Oct. 21, 1992, now abandoned, which is a continuation division of application Ser. No. 07/635,746, filed Dec. 12, 1990 which is now abandoned, which is a continuation-in-part of U.S. application Ser. No. 07/458,996, filed Dec. 29, 1989, now abandoned which is incorporated herein by this reference.

FIELD OF THE INVENTION

The present invention relates to compositions supplemented with arginine or ornithine, or functional analogs of arginine or ornithine, for enteral administration to human patients, and to amino acid solutions supplemented with arginine or ornithine, or functional analogs of arginine or ornithine, for parenteral administration to human patients, and to methods for formulating and using the compositions and solutions. More particularly, the invention relates to compositions and solutions supplemented with arginine or ornithine, or functional analogs of arginine or ornithine, that are useful for treating an impaired immune response in a human or to inhibit degradation of the immune response in a human who has suffered accidental or surgical trauma or a debilitating disease.

BACKGROUND OF THE INVENTION

Arginine is considered to be a semi-essential amino acid in certain mammals, i.e., while arginine can be synthesized by these mammals, it cannot be synthesized at a rate sufficient to meet the demands of normal growth. In humans, arginine is not growth-limiting and therefore is a non-essential amino acid.

The synthetic pathway for arginine commences with ornithine. Ornithine is combined with carbamyl phosphate to produce citrulline, which in turn is combined with aspartate, in the presence of adenosine triphosphate (ATP), to produce argininosuccinate. In the final step, fumarate is split from argininosuccinate, to produce arginine. The degradative pathway for arginine is by the hydrolytic action of arginase, to produce ornithine and urea. All of the reactions described above form the urea cycle.

Arginine's best-studied functions are in the urea cycle and as an essential amino acid for the synthesis of proteins. However, other functions for arginine have been described. Of particular interest is the effect of arginine and its metabolic precursor, ornithine, on the immune system of immunosuppressed or immune-impaired animals. Since arginine is a component of proteins, it is present in a normal diet. However, ornithine is not a component of proteins and, as a result, it is not present, at significant levels, in a normal diet.

The immune system of mammals is comprised of two kinds of effector mechanisms; the first mechanism is mediated by antibodies and is called "humoral immunity"; the second mechanism is mediated by cells and is called "cell-mediated immunity" (CMI). Most immune responses involve the activity and interplay of both the humoral and the cell-mediated branches of the immune system.

Antibodies, which are molecules that are able to specifically recognize and bind antigens, are found in the blood and lymph and are synthesized in a subset of lymphocytes called "B lymphocytes" or "B cells." CMI, on the other hand, derives its specificity from a subset of lymphocytes called "T lymphocytes" or "T cells."

The development of a normal CMI response requires a functional thymus. In humans, as well as in other mammals, the thymus reaches its maximal size at about the age of puberty. Thereafter, it shrinks or involutes, and much of its architecture is replaced by fatty tissue. In old age, the thymus is reduced to a tiny, fatty rudiment. However, despite the age-related involution, aged thymuses retain some function. Stress is one factor which results in thymus involution. The probable mechanism of stress involution of the thymus, where disease or other stresses lead to rapid shrinking of the thymus, is the stress-triggered releases of corticosteroids from the adrenal cortices. The thymus is very sensitive to this group of hormones (corticosteroids), and injection of a corticosteroid, such as cortisol, leads to rapid (within hours) involution of the thymus of experimental animals.

The main function of the thymus in CMI is to produce mature T lymphocytes, the cells that carry out CMI. T lymphocytes are made up of a number of subsets of lymphocytes which have specialized functions. Of particular interest are two subsets of lymphocytes called "T suppressor cells" (Ts) and "T helper cells" (Th). The Ts cell subsets are responsible for suppression of both humoral immune reactions and CMI reactions. Ts cells differ from the other subsets of T cells in being able to bind to soluble antigen. The Th subsets are required to assist B cells to mount a humoral response to certain antigens.

The ability of an animal to mount an immune response, both humoral and cell-mediated, is called immunocompetence and is critical for fighting off infection. However, under certain conditions, such as trauma, surgery, certain viral infections, and cancer, an animal's ability to fight infection is impaired (an impaired immune response is also called immunosuppression) and sepsis results.

A measure of the ability of an immune system to respond normally can be made by evaluating the ratio of Th cells to Ts cells in the blood. For example, a Th/Ts ratio of less than about 1 is considered to be an indicator of an impaired immune response in humans.

The activity of T lymphocytes in vivo has been found to correlate with their in vitro response to mitogens, which are a variety of chemical substances which bind to the surface of lymphocytes and, in doing so, stimulate them to undergo mitosis. Mitosis is an important indicator of immune function, since T cells have to replicate (a process known as clonal expansion) in order to carry out their immune functions. A measure of the ability of cells to undergo mitosis is the stimulation index, which is the ratio of the mean number of cells in the presence of a mitogen to the mean number of control, or unstimulated, cells. Commonly, the number of cells is estimated by labeling them with radio-labeled thymidine and measuring counts per minute (as an assay of DNA content, which is directly correlated with cell numbers). Stimulation index is therefore calculated by the ratio of counts per minute of mitogen-stimulated cells divided by counts per minute of unstimulated cells. A low stimulation index is another indicator of an impaired immune response. For example, when the stimulation index is reduced to below approximately 50% of its normal value, the immune response can be considered to be impaired.

Several lymphocyte mitogens are plant-derived glycoproteins (lectins) that bind specifically to certain sugar residues of glycoproteins on the cell surface. Two such lectins are Phytohemagglutin (PHA) and Concanavalin A (ConA).

PHA, extracted from the red kidney bean, binds to both B and T lymphocytes. However, it only stimulates mitosis in mature cells. ConA, extracted from the jack bean, has a strong mitogenic effect on T cells, immature as well as mature, but not on B cells.

Dietary arginine supplementation has been used to treat rats and mice that have been subjected to trauma. In such animals, arginine has been observed to produce an increase in thymic weight, an increase in the number of lymphocytes present in the thymus, an increase in the response of lymphocytes to mitogens, a positive effect on virus-induced tumors where the virus was thymolytic and the subsequent damage to the thymus allowed for the initial tumor expression, an increase in weight gain, and enhancement of wound healing. Citrulline, a metabolic precursor of arginine, can replace arginine for growth requirements, but has been found to have no detectable effect on thymus function, i.e., has no thymotropic action. Ornithine, another metabolic precursor of arginine, exhibits the thymotropic effect of arginine without being able to replace it for growth requirements.

It has been suggested that the positive effects of arginine on wound healing are mediated via an intact thymus, and the beneficial effects of supplemental arginine in animal tumor models appear to correlate with its thymotropic effect. The positive effect of arginine on these animals' immune systems has been proposed to be due, in part, to arginine's well-known secretory-inducing activity on pituitary and pancreatic hormones, particularly on growth hormone. Growth hormone also leads to an increase in thymic weight and, therefore, cell-mediated immunity.

Although there have been major advances in the care of severely ill patients, such as new antibiotics, nutritional support, and developments in critical-care medicine, many ill patients still die due to sepsis. Such sepsis occurs as a result of an impaired immune response that is either pre-existing or which occurs as a result of the illness that initially caused the patient to be admitted to the hospital. The most common causes of such an impaired immune response in severely ill patients are trauma, major surgical procedures, malnutrition, cancer, old age, and infection with HIV (AIDS) virus.

Previously, nutritional supplementation of severely ill patients has been used to maintain a patient's body protein stores in an attempt to counteract the protein breakdown (catabolism) that such patients suffer. Although this nutritional supplementation is often successful in reversing the catabolic process and can even stimulate some anabolic processes, such as wound healing, in many cases, it has not been shown to reverse the impaired immune response exhibited by these patients. These patients remain at risk of sepsis and death, in spite of nutritional supplementation. Therefore, a safe and effective nutritional means of restoring the immune response would be beneficial to the long-term survival of these severely ill patients.

SUMMARY OF THE INVENTION

The present invention relates to methods for treating the human immune response and to compositions and solutions supplemented with arginine or ornithine, or functional analogs of arginine or ornithine, used for enteral and parenteral administration for effecting the treatment.

In one embodiment, a method is provided for reducing the severity of degradation of the immune response in a human who has suffered accidental or surgical trauma or a debilitating disease, which comprises administering to a human who has suffered accidental or surgical trauma or a debilitating disease, a therapeutically effective amount of arginine or ornithine or a functional analog of arginine or ornithine or mixtures thereof, alone or in combination with other nutrients, in an amount greater than the amount of arginine present in the normal diet or in a normal parenteral nutritional regimen.

In another embodiment, a method is provided for treating an impaired human immune response, which comprises administering to a human with an impaired immune response, a therapeutically effective amount of arginine or ornithine or a functional analog of arginine or ornithine or mixtures thereof, alone or in combination with other nutrients, in an amount greater than the amount of arginine present in the normal diet or in a parenteral nutritional regimen.

The amount of arginine present in the "normal enteral diet," as used herein, is no more than about 7.4 grams per day, and in a "normal parenteral nutritional regimen," as used herein, is no more than about 12 grams per day. As used herein, "enteral" means administration into the intestines either orally or by catheter, etc. Significant levels of ornithine are not present in a normal enteral diet or in a normal parenteral nutritional regimen.

DETAILED DESCRIPTION

The process of this invention provides a method for treating an impaired human immune response (immunosuppression) or for reducing the severity of the degradation of the immune response in a human. Immunosuppression occurs when the immune system is not functioning normally, thereby resulting in an increased susceptibility to infection, i.e., a suppressed immune responsiveness. An indicator of a suppressed immune function is a reduced number of lymphocytes or reduced lymphocyte function, such as a reduced response to mitogenic stimulation. In accordance with this invention, a human immune system is also considered to be impaired when (1) the ratio of Th/Ts is less than about 1.0, (2) when the stimulation index to ConA is approximately 50% less than "normal," or (3) when the stimulation index to PHA is approximately 50% less than "normal."

An impaired human immune response is frequently observed as a secondary effect of such conditions as trauma, for example, from an accident or from undergoing a major surgical procedure, from a debilitating disease, such as cancer or infection with the HIV virus (AIDS), or from malnutrition or old age. As a result of an impaired immune response, patients are unable to respond to and eliminate infectious agents, such as bacteria, viruses, and fungi, from their bodies. The resultant, unchecked infection leads to sepsis, which can result in the death of the patient. Compounds such as arginine or ornithine or a functional analog of arginine or ornithine or mixtures thereof, are a safe and non-toxic means of correcting a pre-existing impaired immune responses in humans and can reduce the severity of the degradation of the immune response in a human who, for example, has suffered accidental or surgical trauma or a debilitating disease, is severely malnourished, or is old. As used herein, an "accidental trauma" means an injury such as a bone fracture, extensive and severe soft-tissue injury, a burn injury, or the like, which results in the need for hospitalization or in increased risk of infection (sepsis) and/or death. A "surgical trauma" as used herein means major surgical procedures on the gastrointestinal tract, vascular system, or other systems where the patient is at a higher risk for developing post-operative infectious complications. A "debilitating disease" as used herein means a disease such as cancer, infection with HIV, or infection with other agents which may result in multiple-system organ failure.

The present invention comprises administering to a human with an impaired immune response or to one who has been subjected to an accidental or surgical trauma or who is suffering from a debilitating disease or old age, or is severely malnourished, a supplement of arginine or ornithine or a functional analog of arginine or ornithine or mixtures thereof, in quantities greater than those found in the normal oral (also called "enteral") diet or in a normal parenteral nutrition regimen, in addition to nutrients required for good nutrition of a normal individual. The supplement may be administered enterally or parenterally. The term "enteral" or "enterally" means administration into the gut, either orally or via tube feeding procedures such as via a nasogastric, nasointestinal, esophagostomy, gastrostomy, or jejunostomy feeding tubes. "Parenterally" means via intravenous or IV administration. As used herein, the terms "arginine" and "ornithine" refer to their free bases. The phrase "functional analogs of arginine or ornithine" refers to salts of arginine or ornithine, peptides containing arginine or ornithine, and derivatives of arginine or ornithine which retain the functional characteristics of arginine or ornithine in the treatment of an impaired immune response or in reducing the severity of degradation of the immune response in a human who has suffered accidental or surgical trauma or a debilitating disease.

In a preferred embodiment of practice of the present invention, arginine or ornithine or a functional analog of arginine or ornithine or mixtures thereof, is administered in a sufficient amount to provide the individual with a total intake of at least about 15 grams per day. This is an amount which is at least about 8 grams per day more than the maximum amount of arginine present in the normal oral diet, and at least about 3 grams per day more than the maximum amount present in the normal parenteral nutritional regimen. When a functional analog of arginine or ornithine is provided, the therapeutically effective amount is based on the proportional weight of arginine or ornithine comprising the compound. For example, when arginine provides 50% of the weight of an arginine-containing peptide, the therapeutically effective amount of the peptide is a supplement comprising at least about 30 g per day.

The normal oral daily intake of arginine, which is a naturally occurring amino acid found in most proteins, is from about 1.2 g to about 7.4 g per day (based on an average arginine content in proteins of from about 3.1% (wt/wt) to about 10.6% (wt/wt) and a daily intake of protein of from about 40 g to about 70 g). The term "% (wt/wt)" as used above means the weight of arginine per 100 g of total protein. The preferred therapeutically effective amount of at least about 8 g of arginine or ornithine or a functional analog of arginine or ornithine or mixtures thereof per day, in addition to the normal oral diet, is a large increase in the normal daily dietary intake of this amino acid. To obtain the desired high levels of arginine or ornithine or a functional analog of arginine or ornithine or mixtures thereof, supplementation of the normal oral diet with arginine or ornithine or a functional analog of arginine or ornithine or mixtures thereof, in accordance with practice of this invention is required. The alternative to supplementation would be the ingestion of protein sources having at least about 21% (wt/wt) arginine (based on 70 g daily protein intake) to achieve the desired 8 g per day arginine above the normal dietary amount for a total arginine intake of at least 15 g per day. No naturally occurring dietary proteins have such high concentrations of arginine. A second alternative would be to increase the dietary intake of protein, which would require increasing the daily amount of ingested protein by at least about 80 g per day (based on a protein with a 10% (wt/wt) arginine content). Neither of these alternatives is practical, therefore, supplementation in accordance with this invention is required.

Ornithine is a naturally occurring amino acid, but is not a component of proteins, as is arginine. Ornithine is synthesized by the body from glutamic acid and is a precursor for the synthesis of other compounds, such as arginine. Since ornithine cannot be obtained readily from dietary proteins, the high levels of ornithine needed to treat an impaired immune response must be derived solely from a dietary supplement.

Total parenteral nutrition (TPN) is defined by the nutritional formulae used for patients who derive their entire dietary requirements intravenously. Arginine is contained in most TPN solutions, such as those supplied by McGaw, Inc. under the trademarks "FREAMINE II," which contains 0.31 g of arginine per 100 ml; "HEPTAMINE," which contains 0.6 g of arginine per 100 ml; "TROPHAMINE," which contains 0.732 g of arginine per 100 ml; and "FREAMINE III," which contains 0.8 g of arginine per 100 ml. These solutions are typically administered at a rate of about 1.5 l per day, which results in a daily arginine intake of up to 12 g per day. This amount is defined as the normal TPN diet. None of the TPN solutions contains ornithine. Therefore, therapeutic amounts of this amino acid can only be derived from supplementation of the TPN solutions. Administration of the preferred amounts of arginine or ornithine or a functional analog of arginine or ornithine or mixtures thereof, provided in accordance with this invention is achieved by supplementing the normal TPN diet with a therapeutically effective amount of arginine or ornithine or a functional analog of arginine or ornithine or mixtures thereof. This can be accomplished by providing an increased amount of arginine in the TPN solution or by adding ornithine or a functional analog of arginine or ornithine to the solution, or can be provided by parenterally administering a supplement in addition to the administration of a previously available TPN solution.

In accordance with practice of the present invention, preferably, the amount of arginine or ornithine or a functional analog of arginine or ornithine or mixtures thereof administered per day to the individual undergoing TPN is sufficient to provide the individual with a total daily intake of from between about 15 g and about 35 g per day. Thus, for example, when arginine is used as the supplement to a TPN regimen that is designed to provide about 12 g of arginine per day, the total amount of arginine provided is at least about 15 g. If, for example, ornithine, or a functional analog of arginine or ornithine or mixtures thereof, is used in combination with a TPN solution that supplies 12 g of arginine per day, at least 3 g of ornithine, or a functional analog of arginine or ornithine or mixtures thereof, will be used. This will result in a total combination of arginine or ornithine, or a functional analog of arginine or ornithine or mixtures thereof, of at least about 15 g per day.

Administration of arginine or ornithine or a functional analog of arginine or ornithine or mixtures thereof that results in a total intake of less than about 15 g per day confers little or no beneficial effects on the immune system of the patient as determined by thymus mass, numbers of lymphocytes, and stimulation of lymphocytes by mitogens.

In a preferred embodiment of this invention, a normal oral diet or a normal TPN diet is supplemented with arginine or ornithine, or a functional analog of arginine or ornithine or mixtures thereof, to result in a total intake of arginine or ornithine, or a functional analog of arginine or ornithine or mixtures thereof, of between about 15 g and about 35 g per day.

The dietary supplementation with arginine or ornithine, or a functional analog of arginine or ornithine or mixtures thereof, may be provided either enterally or parenterally. When arginine or ornithine, or a functional analog of arginine or ornithine or mixtures thereof, are provided as an oral supplement to an enteral diet, it is preferable to give the supplement in divided doses since ingestion of the total daily dose at once may result in diarrhea, mild nausea, or other minor side-effects. When arginine or ornithine, or a functional analog of arginine or ornithine or mixtures thereof, are provided as an intravenous supplement to an enteral diet, it is preferable to give the supplement at a rate of about 500 ml per day for a solution that contains from 6 g to 60 g/l of arginine, ornithine or a functional analog of arginine or ornithine or mixtures thereof. As mentioned above, the administration may also be made via TPN.

Arginine Supplement Composition for Enteral Administration

The arginine supplement compositions provided in accordance with practice of the present invention for enteral administration (either via oral or tube feeding) preferably include other essential and non-essential amino acids in addition to arginine. For example, in a preferred composition, isoleucine (Ile), leucine (Leu), lysine (Lys), methionine (Met), phenylalanine (Phe), tryptophan (Trp), threonine (Thr), valine (Val), and histidine (His) are included as essential amino acids, while alanine (Ala), proline (Pro), glycine (Gly), serine (Ser), tyrosine (Tyr), glutamic acid (Glu), glutamine (Gln), aspartic acid (Asp), cysteine (CysH/Cys), and taurine (Tau) are included as non-essential amino acids.

The amino acids used in the compositions and solutions of the present invention are preferably pure amino acids. In general, the amino acids should be in their L-form rather than the D-form or mixture of D- and L-forms. Also, in general, the amino acids are employed as free amino acids, but can be as amino acids salts or derivatives. For example, L-lysine acetate may be used, and derivatives of L-tyrosine, which are converted to tyrosine in the body, may also be used. Other examples include the keto acid analogs, di-peptides, tri-peptides, and N-acetyl derivatives of the various amino acids. In addition, it is convenient to incorporate cysteine in the form of its hydrochloride salt (L-cysteine HCL.H2O).

One embodiment of an amino acid composition or formulation for enteral administration provided in accordance with the present invention includes the following amino acid concentrations in terms of % weight of individual amino acids to the total weight of the amino acids in the composition (% w/w).

TABLE 1

| Amino Acids | % w/w |
| --- | --- |
| L-isoleucine | 8.6 |
| L-leucine | 15.2 |
| L-lysine | 4.6 |

TABLE 1-continued

| Amino Acids | % w/w |
| --- | --- |
| L-methionine | 1.2 |
| L-phenylalanine | 1.5 |
| L-tryptophan | 0.9 |
| L-threonine | 2.4 |
| L-valine | 11.2 |
| L-arginine | 18.7 |
| L-histidine | 0.7 |
| L-alanine | 2.6 |
| L-proline | 2.1 |
| Glycine | 0.9 |
| L-serine | 1.9 |
| L-tyrosine | 1.7 |
| L-glutamic Acid | 8.3 |
| L-glutamine | 11.2 |
| L-aspartic Acid | 5.3 |
| L-cysteine | 0.8 |
| Taurine | 0.3 |

The relative proportion of each individual amino acid can vary about ±15% while providing a composition useful in accordance with practice of the present invention.

In one exemplary embodiment of the arginine supplement composition shown in Table 1, the composition preferably includes the following amounts of amino acids in grams:

TABLE 2

| Amino Acids | Grams |
| --- | --- |
| L-isoleucine | 3.0–4.0 |
| L-leucine | 5.2–7.0 |
| L-lysine | 1.5–2.1 |
| L-methionine | 0.4–0.6 |
| L-phenylalanine | 0.5–0.7 |
| L-tryptophan | 0.3–0.7 |
| L-threonine | 0.8–1.0 |
| L-valine | 3.8–5.2 |
| L-arginine | 6.4–8.6 |
| L-histidine | 0.2–0.4 |
| L-alanine | 0.9–1.1 |
| L-proline | 0.7–0.9 |
| Glycine | 0.3–0.5 |
| L-serine | 0.7–0.9 |
| L-tyrosine | 0.6–0.8 |
| L-glutamic Acid | 2.8–3.8 |
| L-glutamine | 3.8–5.2 |
| L-aspartic Acid | 1.8–2.4 |
| L-cysteine | 0.2–0.4 |
| Taurine | 0.1–0.2 |

The absolute values of the weights of amino acids contained in the composition is not critical in that compositions of more or less total weight can obviously be used. It is significant and important, however, that the relative weights or proportions of the amino acids to one another be maintained. Thus, if twice the amount of the composition is provided, the amount of the preferred range of the amount of each amino acids is doubled. Regardless of the absolute values for the weight of the amino acids in a composition, any composition that has the relative proportion of its amino acids the same as the relative proportion of the amino acids shown for the composition of Table 2, falls within the scope of the compositions of this invention.

The arginine supplement composition containing the amino acids shown in Table 2 is enterally administered to a human with an impaired immune response. Such enteral administration can be by means of oral administration or by means of tube feeding, and the amount of the composition administered is preferably such that the total amount of amino acids administered to the patient per day is shown below in Table 3.

TABLE 3

| Amino Acids | Grams/Day |
|---|---|
| L-isoleucine | 12.0–16.0 |
| L-leucine | 20.8–28.0 |
| L-lysine | 6.0–8.4 |
| L-methionine | 1.6–2.4 |
| L-phenylalanine | 2.0–3.0 |
| L-tryptophan | 1.2–2.0 |
| L-threonine | 3.2–4.0 |
| L-valine | 15.2–21.0 |
| L-arginine | 15.0–35.0 |
| L-histidine | 0.8–1.6 |
| L-alanine | 3.6–4.4 |
| L-proline | 2.8–3.6 |
| Glycine | 1.2–2.0 |
| L-serine | 2.8–3.6 |
| L-tyrosine | 2.4–3.2 |
| L-glutamic Acid | 11.2–15.2 |
| L-glutamine | 15.2–20.8 |
| L-aspartic Acid | 7.2–9.6 |
| L-cysteine | 0.8–1.6 |
| Taurine | 0.4–0.8 |

The amino acids contained in the arginine supplement composition for enteral administration provided in accordance with the present invention can include other ingredients for nutrition. For example, fats and oils, carbohydrates, vitamins and dietary minerals. The components of one such exemplary composition are shown in the following table in amounts shown for each portion or package.

TABLE 4

| Ingredient | Grams |
|---|---|
| Protein (Lactalbumin) | 18.5 |
| Added Amino Acids | |
| L-arginine | 7.0 |
| L-glutamine | 4.5 |
| L-leucine | 3.6 |
| L-isoleucine | 2.7 |
| L-valine | 3.7 |
| Carbohydrate | 60.0 |
| Fat | 11.0 |
| Vitamins and minerals | 5.7 |

In the composition shown in Table 4, various amino acids are provided by 18.5 grams of Lactalbumin in addition to the "added amino acids" shown in Table 4 to provide that the total amino acids in the composition are as follows:

TABLE 5

| Amino Acids | Grams of Amino Acid From 18.5 g of Lactalbumin | Grams of "Added Amino Acids" | Grams of Amino Acids (Total) |
|---|---|---|---|
| Ile | 0.8 | 2.7 | 3.5 |
| Leu | 2.5 | 3.6 | 6.1 |
| Lys | 1.8 | | 1.8 |
| Met | 0.5 | | 0.5 |
| Phe | 0.6 | | 0.6 |
| Try | 0.4 | | 0.4 |
| Thr | 0.9 | | 0.9 |
| Val | 0.8 | 3.7 | 4.5 |
| Arg | 0.5 | 7.0 | 7.5 |
| His | 0.3 | | 0.3 |
| Ala | 1.0 | | 1.0 |
| Pro | 0.8 | | 0.8 |
| Gly | 0.4 | | 0.4 |
| Ser | 0.8 | | 0.8 |
| Tyr | 0.7 | | 0.7 |
| Glu | 3.3 | | 3.3 |
| Gln | 0.0 | 4.5 | 4.5 |
| Asp | 2.1 | | 2.1 |
| Asn | 0.0 | | 0.0 |
| CysH/Cys | 0.3 | | 0.3 |
| Tau | 0.0 | 0.1 | 0.1 |

Lactalbumin such as that useful in accordance with the present invention can be provided by New Zealand Milk Products, Inc. of Petaluma, Calif., under the trademark "ALATAL 825."

The fats in one embodiment include 5.5 g of canola oil, such as that provided by Calgene Chemical Company of Des Plaines, Ill., under the trademark "AGRO 0101," and 5.5 g of medium chain triglycerides. The carbohydrates in one embodiment include maltodextrose provided by Grain Processing Corporation of Muscatine, Iowa, under the trademark MALTRIN 50 and MALTRIN 100.

The arginine supplement composition may be provided in dry or powder form incorporating flavorings and emulsifiers so that it may be reconstituted into a liquid (for example, an aqueous emulsion) for enteral administration.

In another preferred embodiment of the amino acid supplement composition shown in Table 1, the composition includes the following amounts of amino acids and other ingredients in grams.

TABLE 6

| | Grams |
|---|---|
| Amino Acids | |
| L-isoleucine | 3.5 |
| L-leucine | 6.1 |
| L-lysine | 1.8 |
| L-methionine | 0.5 |
| L-phenylalanine | 0.6 |
| L-tryptophan | 0.4 |
| L-threonine | 0.9 |
| L-valine | 4.5 |
| L-arginine | 7.5 |
| L-histidine | 0.3 |
| L-alanine | 1.0 |
| L-proline | 0.8 |
| Glycine | 0.4 |
| L-serine | 0.8 |
| L-tyrosine | 0.7 |
| L-glutamic Acid | 3.3 |
| L-glutamine | 4.5 |
| L-aspartic Acid | 2.1 |
| L-cysteine | 0.3 |
| Taurine | 0.1 |
| Other Ingredients | |
| Maltodextrose | 49.0 |
| (MALTRIN M50 and M100) | |
| Mineral Premix* | 10.9 |
| Canola Oil | 5.5 |
| Medium Chain Triglycerides | 5.5 |
| Yeast Extract | 3.9 |
| Citric Acid | 2.9 |
| Vitamin Premix** | 2.8 |
| Soy Lecithin | 0.6 |
| Custard Flavor | 0.6 |
| Gelcarin | 0.5 |

TABLE 6-continued

|  | Grams |
|---|---|
| Aspartame | 0.3 |
| Choline Bitartrate | 0.2 |
| Panalite | 0.2 |
| Oleoresin Cinnamon | 0.2 |
| L-Carnitine | 0.05 |
| Eggshade | 0.01 |

*The mineral premix, in one embodiment, comprises the following ingredients in a % w/w basis.

TABLE 6a

| Maltodextrose (MALTRIN M100) | 50.00000000 |
|---|---|
| Potassium Citrate H$_2$O | 24.57100000 |
| Sodium Chloride | 10.37000000 |
| Dicalcium Phosphate | 6.85710000 |
| Monocalcium Phosphate | 5.71420000 |
| Magnesium Oxide | 1.78280000 |
| Ferrous Gluconate 2 H$_2$O | 0.42285000 |
| Zinc Oxide | 0.15856000 |
| Copper Gluconate Anhydrous | 0.07314200 |
| Manganous Sulfate H$_2$O | 0.03926800 |
| Sodium Molybdate | 0.00097142 |
| Sodium Fluoride | 0.00756570 |
| Chromium Chloride | 0.00065600 |
| Selenium Dioxide | 0.00073142 |
| Potassium Iodide | 0.00051428 |

**The vitamin premix, in one embodiment, comprises the following ingredients on a % w/w basis.

TABLE 6b

| Component | % w/w |
|---|---|
| Maltodextrose (MALTRIN M100) | 90.6210000 |
| Ascorbic Acid | 5.4713000 |
| dl-alpha-tocophryl Acetate | 2.3253000 |
| Bitrit (1% Biotin) | 0.3588600 |
| Vitamin A Palmitate (1 µg = 0.25 IU) | 0.1658400 |
| Niacinamide | 0.2265500 |
| Phytonadione (1% SD) | 0.1105600 |
| d-Calcium Pantothenate | 0.1359300 |
| Vitamin B$_{12}$ (0.1% SD) | 0.0724970 |
| β-Carotene (1 IU-6 µg, 10%) | 0.1087500 |
| Vitamin D$_3$ (100 IU/mg) | 0.0521070 |
| Pyridoxine HCL | 0.3026700 |
| Thiamine Mononitrate | 0.0208430 |
| Riboflavin | 0.0208430 |
| Folic Acid | 0.0065247 |

Arginine Supplement Composition for Parenteral Administration

The arginine supplement compositions provided for parenteral administration preferably include other essential and non-essential amino acids in addition to arginine. For example, in a preferred composition, isoleucine (Ile), leucine (Leu), lysine (Lys), methionine (Met), phenylalanine (Phe), tryptophan (Trp), threonine (Thr), and histidine (His) are included as essential amino acids, while alanine (Ala), proline (Pro), glycine (Gly), serine (Ser), tyrosine (Tyr), glutamic acid (Glu), aspartic acid (Asp), cysteine (CysH/Cys), and taurine (Tau) are included as non-essential amino acids.

The concentrations of amino acids listed in Table 7 below are for the purpose of illustrating preferred aqueous amino acid solutions provided in accordance with the present invention for arginine supplementation. It should be understood that different concentrations may be used provided the relative concentrations of amino acids remain as set forth in the table.

TABLE 7

| Amino Acids | Concentration In w/w % |
|---|---|
| L-isoleucine | 8.7 |
| L-leucine | 15.3 |
| L-lysine.Ac (Lys Eq) | 6.8 |
| L-methionine | 7.2 |
| L-phenylalanine | 4.2 |
| L-tryptophan | 2.9 |
| L-threonine | 4.8 |
| L-valine | 11.3 |
| L-arginine | 14.1 |
| L-histidine | 3.4 |
| L-alanine | 3.9 |
| L-proline | 4.9 |
| Glycine | 1.2 |
| L-serine | 2.8 |
| L-tyrosine | 0.5 |
| N-acetyl-L-Tyr | 2.4 |
| L-glutamic Acid | 2.6 |
| L-aspartic Acid | 2.4 |
| L-cysteine.HCl.H2O | 0.2 |
| Taurine | 0.4 |

The relative proportion of each amino acid can vary about ±15% while providing a solution useful in accordance with practice of the present invention, i.e., the % w/w can vary ±15% of the % w/w value.

It is understood that, in addition to amino acids, other nutritional ingredients, e.g., carbohydrates, lipids, electrolytes, and vitamins may be included along with preservatives or stabilizers as required, such as sodium bisulfite, ascorbic acid (vitamin C), or other compatible preservative agents. The formulations are desirably free of ammonia. When prepared from desirably free of ammonia. When prepared from crystalline amino acids, the resulting formulation will be low in free ammonia.

The formulations may be advantageously prepared in the form of sterile, aqueous solutions adapted for intravenous, i.e., parenteral, administration. In accordance with known practices for preparing such parenteral solutions, the solutions will be sterile pyrogen-free, and have a suitable pH for intravenous administration. The most desirable pH for the solution may vary, but, in general, the pH of the solution can range from about 5.0 to about 7.8. In most cases where the solution is used for TPN, i.e., no nutrients are taken orally, the solutions described herein can be administered into a central vein, which is the procedure known clinically as hyperalimentation. In this technique, either a subclavian or internal jugular indwelling catheter may be used.

Arginine supplement solutions for parenteral administration preferably contain from about 2.5 to 10.0% w/v total amino acids. In more preferred embodiments, which can be used for total parental nutrition, the optimum concentration is from about 5.0 to about 10.0% w/v. As is mentioned above, such solutions are administered to a human with an impaired immune response, or to a human who has been subjected to an accidental or surgical trauma, or who is suffering from a debilitating disease or from old age, or is severely malnourished, in an amount such that the amount of arginine administered to the patient on a daily basis is at least 15 grams. Preferably, the amount of arginine administered daily is from 15 grams to about 35 grams.

EXAMPLE 1

Arginine Stimulation of Lymphocyte Immune Response in Healthy Human Beings

Twelve normal, healthy, human volunteers were given oral supplements of 30 g of arginine HCl per day for 7 days in addition to their normal food intake. (The amount of arginine supplemented per se was approximately 25 grams per day, i.e., about 5 grams was from the HCl moiety.) The arginine HCl was in the form of a powder which was packaged in gelatin capsules (20 to 23 capsules were ingested per day) to mask the strong and unpleasant aftertaste of arginine. The time of administration was not regulated, and the volunteers were instructed to ingest the daily prescribed amount over each 24-hour period. The normal dietary intake of the volunteers was ad libitum, and no restrictions were placed on the types or times of the food ingested.

On day one (the day prior to the start of arginine supplementation) and on day eight (the seventh day of daily ingestion of arginine), peripheral venous blood was obtained from the volunteers after an overnight fast. Samples were obtained and blood counts, levels of calcium, phosphorus, glucose, blood urea nitrogen, uric acid, cholesterol, total proteins, albumin, bilirubin, alkaline phosphatase, lactic dehydrogenase, and serum glutamic oxaloacetic transaminase were determined. In addition, about 5 ml of heparinized venous blood (containing about 25 units of heparin per ml of blood) was obtained for lymphocyte studies. For the lymphocyte studies, the blood was kept at room temperature and used within 4 hours. A quantity of 100 ul of phosphate-buffered saline (PBS), which contained no calcium or magnesium, was dispensed into labelled, siliconized, 100×13 mm tubes. For each blood sample, a negative control which consisted of PBS was included. Well-mixed blood (100 ul) was added to each tube containing PBS, followed by 10 ul of the appropriate monoclonal antibody. The appropriate monoclonal antibodies used were: anti-Leu-4 (CD3) FITC, for all T cells; anti-Leu-3a (CD4) FITC for T helper-inducer cells; and anti-Leu-2a (CD8) FITC for cytotoxic/suppressor cells, and were obtained from Beckton Dickinson of Mountainview, Calif. The reaction tubes were mixed by vortexing for 2 seconds, covered, and incubated at 2° C. to 4° C. for about 45 minutes to about 1 hour in the dark. During the incubation period, the tubes were shaken every 15 min. At the end of the incubation period, 3 ml of PBS was added to each tube to wash the blood cells.

The blood cells were separated from the wash solution by centrifugation at 200×g in a refrigerated centrifuge with swinging buckets for about 4 to about 5 minutes at 4° C. The supernatant was aspirated, leaving behind approximately 100 ul of fluid and the packed blood-cell pellet. The blood-cell pellet was vortexed and rewashed with an additional 3 ml of PBS. The blood cells were recovered by centrifugation, as described above. The washed blood-cell pellet was mixed by vortexing. Red blood cells that were present in the washed cell pellet were lysed and fixed with "WHOLE BLOOD QUICK STAINING LYSING REAGENTS," supplied by Coulter Immunology of Hialeah, Fla. The final lymphocyte pellet was diluted to from about 0.5 to about 1 ml with PBS and kept in the dark and refrigerated until analyzed. Percentage-staining, which is the number of positive-labelled cells vs. total number of cells, was assessed by flow cytometry using a "FACStar" Counter from Beckton Dickinson Immunocytochemistry Systems of Mountainview, Calif.

The results are summarized in Table 8.

TABLE 8*

| | Pre-Arginine | Post-Arginine | p |
|---|---|---|---|
| T lymphocytes | 1,594 ± 567 | 1,621 ± 425 | NS |
| % T lymphocytes | 71.3 ± 8.9 | 70.2 ± 11.6 | NS |
| T helper | 1,017 ± 525 | 1,072 ± 382 | NS |
| % helper | 50.5 ± 11.7 | 47.9 ± 10.9 | NS |
| T suppressor | 562 ± 122 | 437 ± 118 | <0.05 |
| % T suppressor | 28.3 ± 10.4 | 19.9 ± 5.0 | <0.05 |
| Th/Ts | 1.86 ± 0.73 | 2.55 ± 0.88 | <0.03 |

*Results are the mean ± standard deviation.
NS = Difference between the pre-arginine and post-arginine values was not statistically significant.

The arginine supplementation significantly decreased the T suppressor subset from about 562 to about 437. This decrease resulted in a significant increase in the Th/Ts ratio from about 1.86 to about 2.55. No ill side effects or changes in serum electrolyte or liver function tests were noted during the study.

EXAMPLE 2

Ornithine Stimulation of Lymphocyte Immune Response in Healthy Human Beings

Six normal, healthy, human volunteers were given oral supplements of 30 g per day of ornithine HCl for days, in addition to their normal food intake. (The amount of ornithine supplemented per se was approximately 24 grams per day, i.e., about 6 grams was from the HCl moiety.) The ornithine HCl was in the form of a powder which was packaged in gelatin capsules (20 to 23 capsules were ingested per day) to mask its strong and unpleasant aftertaste. The time of administration was not regulated, and the volunteers were instructed to ingest the daily prescribed amount over each 24-hour period. The normal dietary intake of the volunteers was ad libitum, and no restrictions were placed on the types or times of the food ingested.

On day one (the day prior to ornithine supplementation) and on days four and eight, (the third and seventh days of daily ingestion of ornithine), peripheral venous blood was obtained from the volunteers after an overnight fast. Samples were obtained, and blood counts, levels of calcium, phosphorus, glucose, blood urea nitrogen, uric acid, cholesterol, total proteins, albumin, bilirubin, alkaline phosphatase, lactic dehydrogenase, and serum glutamic oxaloacetic transaminase were determined. In addition, 10 ml of peripheral venous blood was obtained and the serum removed for use in the cell culture studies described below.

Peripheral blood lymphocyte responses to ConA, PHA, and mixed lymphocyte reactions (MLR) were assayed for the blood samples obtained on days one, four, and eight. Fifty ml of heparinized venous blood containing 25 units of heparin per ml of blood was obtained from the volunteers for each of the time points, i.e., days one, four, and eight. The blood was kept at room temperature and used within 2 hours. Equal volumes of well-mixed, heparinized whole blood and SEPRACELL-MN, supplied by Sepratech Corp. of Oklahoma City, Okla., were added to centrifuge tubes and mixed gently by inverting the tubes several times. SEPRACELL-MN is a dense-sugar solution for separation of the mononuclear cells (MNC) from the whole blood on a basis of their buoyant density (which relates to the size of the cells). The tubes were centrifuged at room temperature for 30 min at 1500×g using a swinging bucket rotor. After separation, the MNC band at the surface was removed and washed twice in "RPMI 1640" cell culture medium, supplied by GIBCO of Grand Island, N.Y., (supplemented with 50 U penicillin/ml, 50 ug streptomycin/ml, and 2 mM glutamine) containing 10% heat-inactivated fetal bovine serum (RPMI-BSA) by resuspending the MNC in RPMI-BSA and collecting the MNC by centrifugation. The washed MNC pellet was resuspended in about 10 ml of RPMI 1640 cell culture medium.

Viable mononuclear cells were counted by their Trypan Blue exclusion in a solution of RPMI 1640 supplemented with 0.04% by weight of Trypan Blue in a hemocytometer. Viability always exceeded 90%. Viable mononuclear cells, $1 \times 10^6$ cells/ml, were resuspended in cell culture medium which was supplemented with 10% (vol/vol) autologous serum obtained from the subject on the day of the study, or pooled AB human serum. The term "% (vol/vol)" is the volume of serum added per 100 ml of cell culture medium. The serum was heat-treated for 10 minutes at 56° C. and filtered through a 0.22 u filter supplied under the trade name MILLIPORE by Millipore Corp. of Bedford, Mass., prior to use. Aliquots of cells (0.2 ml) were dispensed into flat microtiter plates to give $0.2 \times 10^6$ cells per microtiter plate well. The "control wells" received an additional 10 ul of serum-supplemented cell culture medium. The "ConA" wells received sufficient volumes of a solution of ConA to give a final amount of ConA of 2 ug and 5 ug per well. The "PHA wells" received sufficient volumes of a solution of PHA to give a final amount of PHA of 20 ug and 40 ug per well. All of the above cultures were performed in triplicate. The microtiter plates containing the cell cultures were incubated at 37° C. in a humid atmosphere of 95% air, 5% $CO_2$. Fifty-five hours later, cultures were "pulsed" by adding 2 uCi of $^3$H(methyl)thymidine with a specific activity of 2 Ci/mM. $^3$H(methyl)thymidine is incorporated into the DNA of rapidly dividing cells. Therefore, the radioactivity derived from $^3$H(methyl)thymidine, incorporated into the cells, is a measure of dividing or doubling rate. After a further 6-hour incubation at 37° C. in a humid atmosphere of 95% air, 5% $CO_2$, cultures were harvested onto fiberglass filters. The cells retained on the filters were rinsed with distilled water to remove any unincorporated $^3$H(methyl)thymidine from the cells. The cell-containing filters were air-dried, suspended in 3 ml of "TRISTA-FLUOR" scintillation fluid (Packard, Bowers Grove, Ill.), and the radioactivity incorporated in the cells was determined in a Packard C2425 Tricarb liquid scintillation spectrometer. The results, expressed as counts per minute (cpm), were averaged for the triplicate cultures. Values are reported as a stimulation index, which is the cpm incorporated into the cells in the presence of a mitogen, divided by the cpm incorporated into the cells in the absence of a mitogen.

The mixed lymphocyte reactions were performed by incubating $5 \times 10^5$ test cells, purified as described above, with $5 \times 10^5$ mitomycin C-inactivated lymphocytes from a single donor. Tritium-labelled thymidine incorporation was measured after 5 days in culture.

The stimulation indices obtained are shown in Table 9.

TABLE 9

| Immune Response of Human Peripheral Blood Lymphocytes | | | |
|---|---|---|---|
| Day | ConA | PHA | MLR |
| 1 | 44.07 ± 37.17 | 170.02 ± 104.17 | 39.4 ± 36.38 |
| 4 | 75.23 ± 73.72 | 212.38 ± 136.18 | 75.43 ± 91.75 |

TABLE 9-continued

| Immune Response of Human Peripheral Blood Lymphocytes | | | |
|---|---|---|---|
| Day | ConA | PHA | MLR |
| 8 | 121.7 ± 58.04* | 336 ± 156.96# | 91.02 ± 73.23 |

*p <0.02 vs. day 0
# p <0.05 vs. day 0

Ornithine supplementation significantly enhanced the mitogenic response of peripheral blood lymphocyte to ConA and PHA after 7 days of ornithine treatment (day eight of the study). MLR levels were higher after 7 days (day eight of the study), but the increase was not statistically significant.

EXAMPLE 3

Immune Stimulation in Patients After Undergoing Surgery

Seven patients undergoing major abdominal surgery and requiring intravenous postoperative nutritional support, were divided into two groups.

Three patients, the control group, received a standard total parenteral nutrition (TPN) mixture consisting of 25% dextrose, and a commercially available amino acid solution sold under the trademark "FREAMINE II" by McGaw, Inc. of Irvine, Calif., as the source of amino acids. The TPN infusate consisting of 25% dextrose, 4.25% amino acids provided by FREAMINE II, electrolytes, vitamins, and trace element was infused at a rate of approximately 125 ml/hour. Intravenous infusions were begun on the first day after surgery. FREAMINE II, the composition of which is given in Table 10, contains 3.1 g arginine/liter, and the amount of arginine infused per day was 4.65 g. In addition to the TPN regimen incorporating FREAMINE II, the control group patients were given 10 grams of essential amino acids in the form of a commercially available amino acid solution sold under the trademark "NEPHRAMINE" by McGaw, Inc. of Irvine, Calif. The composition of NEPHRAMINE, which contains no arginine, is given in Table 11.

Table 12 shows the total daily intravenous intake of the control group of patients.

TABLE 10

| Composition of FREAMINE II | |
|---|---|
| Amino Acid | g/100 ml |
| L-isoleucine | 0.59 |
| L-leucine | 0.77 |
| L-lysine | 0.62 |
| L-methionine | 0.45 |
| L-phenylalanine | 0.48 |
| L-tryptophan | 0.13 |
| L-threonine | 0.34 |
| L-valine | 0.56 |
| L-arginine | 0.31 |
| L-histidine | 0.24 |
| L-alanine | 0.60 |
| L-proline | 0.95 |
| Glycine | 1.70 |
| L-serine | 0.50 |
| L-tyrosine | 0.00 |
| L-glutamic acid | 0.00 |
| L-aspartic acid | 0.00 |
| L-cysteine | 0.014 |

TABLE 11

Composition of NEPHRAMINE

| Amino Acid | g/100 ml |
|---|---|
| L-isoleucine | 0.560 |
| L-leucine | 0.880 |
| L-lysine | 0.640 |
| L-methionine | 0.880 |
| L-phenylalanine | 0.880 |
| L-tryptophan | 0.200 |
| L-threonine | 0.400 |
| L-valine | 0.640 |
| L-histidine | 0.250 |
| L-cysteine | 0.014 |

The control group included: a 47-year-old male undergoing an abdomino-perineal resection; an 81-year-old male undergoing a right hemicolectomy for perforation with peritonitis; and a 71-year-old male undergoing a cholecystectomy, common bile duct exploration, and drainage of a liver abscess.

Four patients, the experimental group, received the same "FREAMINE II" TPN regimen as the control group (without the NEPHRAMINE supplement) and were also given supplementary arginine. Some patients received pre-operative TPN, however, the arginine supplements were begun on the day following the operations (day two). The arginine supplement was given by intravenous infusion at a rate of 10 grams every 8 hours, to give a total of 30 grams per day, in addition to the 4.65 grams provided by the "FREAMINE II" TPN regimen. The total daily intravenous intake of both the control and the experimental groups of patients is shown in Table 12.

TABLE 12

TOTAL DAILY INTRAVENOUS INTAKE
(Amounts are given in grams.)

| Component | Control Patients | Experimental Patients |
|---|---|---|
| Dextrose | 750.0 | 750.0 |
| L-isoleucine | 10.5 | 8.9 |
| L-leucine | 14.2 | 11.6 |
| L-lysine | 11.5 | 9.3 |
| L-methionine | 9.4 | 6.8 |
| L-phenylalanine | 9.8 | 7.2 |
| L-tryptophan | 2.6 | 2.0 |
| L-threonine | 6.3 | 5.1 |
| L-valine | 10.3 | 8.4 |
| L-arginine | 4.65 | 34.65 |
| L-histidine | 4.4 | 3.6 |
| L-alanine | 9.0 | 9.0 |
| L-proline | 14.3 | 14.3 |
| Glycine | 25.5 | 25.5 |
| L-serine | 7.5 | 7.5 |
| L-tyrosine | 0.0 | 0.0 |
| L-glutamic acid | 0.0 | 0.0 |
| L-aspartic acid | 0.0 | 0.0 |
| L-cysteine hydrochloride hydrate | 0.34 | 0.30 |

The experimental group included: a 73-year-old female undergoing esophagectomy; a 45-year-old male undergoing an excision of a pancreatic pseudocyst; a 63-year-old male undergoing an esophagogastrectomy; and a 54-year-old diabetic female on steroids undergoing a Hartmann's procedure for perforated diverticulitis with peritonitis.

The TPN regimens were isonitrogenous, i.e., the nitrogen intake of patients in the experimental group, who were receiving arginine, was the same as the nitrogen intake of the control group.

Blood samples were taken on day one (the day of the surgery), day two (the day after surgery and the day arginine infusion was commenced), and days four and eight (3 and 7 days after arginine infusion was commenced). Blood lymphocytes were harvested and tested for their mitogenic responses to ConA and PHA by the method described in Example 2.

The stimulation indices are shown in Table 13.

TABLE 13

| Stimulation Index at Day | Control | Experimental |
|---|---|---|
| ConA | | |
| 1 | 161.3 ± 77.51 | 166.13 ± 41.04 |
| 2 | 64.73 ± 64.36 | 177.23 ± 71.59 |
| 4 | 38.23 ± 7.18 | 120.5 ± 14.59 |
| 8 | 67.2 ± 17.99 | 149.65 ± 42.13 |
| PHA | | |
| 1 | 161.43 ± 43.13 | 137.55 ± 50.78 |
| 2 | 79.97 ± 19.56 | 80.43 ± 55.22 |
| 4 | 93.77 ± 26.88 | 142.6 ± 47.82 |
| 8 | 97.27 ± 12.84 | 186.65 ± 49.84 |

The results in Table 13 demonstrate that arginine supplementation prevented or lessened the post-operative reduction in mitogenic responses to ConA and PHA.

EXAMPLE 4

The Effect of Arginine Supplementation in Patients Who Are Seropositive for HIV Infections Five patients who were seropositive for HIV infection, i.e., who tested positive for infection with the HIV virus, were selected. These patients had no clinical symptoms referable to their viral infection and had no previous major infectious complications or lymphadenopathy. All patients, as a criterion for entrance into the experimental group, had a Th/Ts ratio less than 0.8. This value was chosen arbitrarily as a sign of an impaired immune response.

The five patients received 20 g of arginine free base per day for a two-week period. The arginine was provided as a powder which was packaged in gelatin capsules (15 to 20 capsules were ingested per day) to mask the strong and unpleasant aftertaste of arginine. The time of administration was not controlled. The normal dietary intake of the volunteers was ad libitum, and no restrictions were placed on the types or times of the food ingested.

Peripheral venous blood was obtained from the patients for lymphocyte studies twice before the start of the arginine supplementation (to ensure stable "baseline values" or pre-treatment control values), at the end of the two-week arginine supplementation, and then at 2 and 6 weeks after the arginine supplementation had been completed. In addition, three patients had peripheral blood lymphocyte mitogenic assays performed at the same times as the lymphocyte studies. The methods used for the lymphocyte studies and the lymphocyte mitogenic assays were the same as those described in Example 1 and Example 2, respectively.

The results are shown in Table 14.

TABLE 14

|  | Pre-Arginine* | End of 2-week Arginine Supple* | 2 Weeks Post Suppl.* | 6 Weeks Post Suppl.* |
|---|---|---|---|---|
| T lymphocytes | 1166 | 1513 | 1423 | 1471 |
| T helper | 347 | 623 | 431 | 476 |
| T suppressor | 745 | 863 | 806 | 887 |

ConA, Stimulation Index

|  | Pre-Arginine | Post-Arginine | 2 Weeks Post | 6 Weeks Post |
|---|---|---|---|---|
| Patient 1 | 2.1 | 14.1 | 19.1 | 26.3 |
| Patient 2 | 5.6 | 16.4 | 24.0 | 37.2 |
| Patient 3 | 7.3 | 14.7 | 21.1 | 9.3 |

PHA, Stimulation Index

|  | Pre-Arginine | Post-Arginine | 2 Weeks Post | 6 Weeks Post |
|---|---|---|---|---|
| Patient 1 | 56.3 | 139.8 | 268.9 | 71.4 |
| Patient 2 | 8.3 | 29.4 | 67.7 | 174.3 |
| Patient 3 | 19.6 | 55.3 | 130.0 | 201.0 |

*The values are mean values for all patients.

No significant changes in T lymphocyte subsets or ratios were discernible following the arginine supplementation. However, a significant enhancement of the mitogenic responses of the lymphocytes to ConA and PHA was observed in all three patients tested. This enhancement persisted for up to six weeks post-supplementation in two patients, while in the third, there was a return to baseline values at that time.

EXAMPLE 5

Enteral Administration of a Preferred Arginine Supplemented Composition In Patients After Undergoing Surgery A dietary supplement composition incorporating the following ingredients on a % w/w basis is prepared.

| Ingredient | % w/w |
|---|---|
| L-Arginine | 5.687 |
| L-Glutamine | 3.648 |
| L-Valine | 3.017 |
| L-Leucine | 2.930 |
| Isoleucine | 2.196 |
| Taurine | 0.08130 |
| Maltodextrin (MALTRIN 050 and 100) | 46.30 |
| Lactalbumin | 15.02 |
| Medium Chain Triglycerides (MCT) | 4.473 |
| Canola oil | 4.473 |
| Yeast Extract | 3.131 |
| Citric Acid | 2.342 |
| Potassium Citrate $2H_2O$ | 2.186 |
| Sodium Chloride | 0.9224 |
| Dicalcium Phosphate | 0.6099 |
| Soy Lecithin | 0.5105 |
| Monocalcium Phosphate | 0.5083 |
| Custard Flavor | 0.4510 |
| Carrageenan (Gelcarin) | 0.3700 |
| Aspartame | 0.2033 |
| Choline Bitartrate | 0.1830 |
| Magnesium Oxide | 0.1586 |
| Mono- and di-glycerides (Panalite) | 0.1356 |
| Oleoresin Cinnamon (Flavor) | 0.1350 |

-continued

| Ingredient | % w/w |
|---|---|
| Ascorbic Acid | 0.1228 |
| dl-α-tocopheryl Acetate | 0.08130 |
| L-Carnitine | 0.04070 |
| Ferrous Gluconate $2H_2O$ | 0.03761 |
| Zinc Oxide | 0.01410 |
| Eggshade (Artificial colors) | 0.01160 |
| Pyridoxine HCl | 0.006791 |
| Copper Gluconate Anhydrous | 0.006506 |
| Niacinamide | 0.005083 |
| Vitamin A Palmitate (1 μg-0.25 IU) | 0.003721 |
| Manganous Sulfate $H_2O$ | 0.003493 |
| d-Calcium Pantothenate | 0.003050 |
| β-Carotene | 0.002440 |
| Vitamin $D_3$ (Cholecalciferol) | 0.001169 |
| Sodium Fluoride | 0.0006730 |
| Riboflavin | 0.0004676 |
| Thiamine Mononitrate | 0.0004676 |
| Folic Acid | 0.0001644 |
| Sodium Molybdate | 0.00008641 |
| Biotin (Bitrit, 1% Biotin) | 0.00008051 |
| Selenium Dioxide | 0.00006506 |
| Chromium Chloride | 0.00005835 |
| Potassium Iodide | 0.00004575 |
| Phytonadione (Vitamin $K_1$ 1% SD) | 0.00002480 |
| Vitamin $B_{12}$ (Cyanocobalamin, 0.1% SD) | 0.000001627 |

Packages each incorporating 123 grams of the composition are provided. The amount of arginine contained in each package is 7.5 grams (0.5 grams from lactalbumin, plus 7.0 grams from added arginine).

410 milliliters of water is poured into a blender, and one package of the arginine supplement composition is added. The blender is turned on at low speed for approximately 30 seconds to form an aqueous emulsion of the arginine composition. If no blender is available, the aqueous emulsion is formed by providing 123 grams of the arginine supplement composition in a wide-bottom bowl and slowing added 410 milliliters of water in approximately 3–4 equal portions, and mixing each portion for about 1 minutes after each addition. Mixing is continued until the liquid becomes homogeneous.

A patient who has undergone an abdomino-perineal resection is fitted with a jejunostomy, gastric, or nasogastric feeding tube. The reconstituted arginine supplement formulation (the 123-gram emulsion) is fed to the patient via the feeding tube at a rate such that total delivery takes from 4 to 5 hours. Administration of the reconstituted supplement is provided 4 times per day, thereby providing the patient with a total amount of arginine of about 30 grams per day. Treatment is continued for as long as required, but not less than 7 days.

EXAMPLE 6

Arginine supplement emulsions are prepared in accordance with Example 5, and an individual who is seropositive for the HIV (AIDS) virus orally ingests the emulsion 3 times per day, thereby providing a daily intake of arginine of 22.5 grams. Treatment is continued for as long as necessary.

EXAMPLE 7

Parenteral Administration of a Preferred Arginine Supplemented Solution

A solution prepared for parenteral administration and which incorporates the following ingredients is provided.

| Amino Acid | Grams/100 ml of Solution |
|---|---|
| Essentials | |
| L-isoleucine | 0.74 |
| L-leucine | 1.30 |
| L-lysine.Ac (Lys Eq) | 0.58 |
| L-methionine | 0.61 |
| L-phenylalanine | 0.36 |
| L-tryptophan | 0.25 |
| L-threonine | 0.41 |
| L-valine | 0.96 |
| Semi-Essentials | |
| L-arginine | 1.20 |
| L-histidine | 0.29 |
| Non-Essentials | |
| L-alanine | 0.33 |
| L-proline | 0.42 |
| Glycine | 0.10 |
| L-serine | 0.24 |
| L-tyrosine | 0.04 |
| N-acetyl-L-tyrosine (Tyr Eq) | 0.20 |
| L-glutamic Acid | 0.22 |
| L-aspartic Acid | 0.20 |
| L-cysteine.HCl.H20 | 0.014 |
| Taurine | 0.032 |
| Phosphoric acid | 0.12 |
| Sodium Bisulfate (Antioxidant) | <0.10 |
| Water for injection | qs |

This solution, in combination with a solution containing carbohydrates, lipids, vitamins and minerals, is administered parenterally to a patient who has undergone a major gastrointestinal surgery. Administration is started on the day after surgery is completed and is continued for as long as necessary, but not less than 14 days. The amount of the solution administered on a daily basis is sufficient to provide the patient with 20 grams of arginine per day. Thus, administration of approximately 1.7 liters per day of the solution is required.

The above descriptions of exemplary embodiments of methods and compositions for treating impaired human immune response and for reducing the severity of degradation of immune response in a human who has suffered accidental or surgical trauma or a debilitating disease, are for illustrative purposes. Because of variations which will be apparent to those skilled in the art, the present invention is not intended to be limited to the particular embodiments described above. The scope of the invention is defined in the following claims.

What is claimed is:

1. An arginine supplemented dietary composition for enteral administration to human patients who have an impaired immune response due to accidental or surgical trauma, or due to old age, or due to severe malnourishment, the composition including the following concentrations of ingredients in terms of w/w %:

| Ingredient | Concentration |
|---|---|
| L-arginine | 6.1% |
| Other essential and non-essential amino acids | 26.5% |
| Fats | 8.9% |
| Carbohydrates | 48.7% |
| Vitamins and Minerals | 4.6% | the remaining ingredients comprising flavorings and emulsifiers.

2. An arginine supplemented dietary composition for enteral administration to human patients who have an impaired immune response due to accidental or surgical trauma, or due to old age, or due to severe malnourishment, the composition including the following concentrations of ingredients in terms of w/w %:

| Ingredient | w/w % |
|---|---|
| Lactalbumin | 15.0 |
| Added Amino Acids | |
| L-arginine | 5.7 |
| L-glutamine | 3.7 |
| L-valine | 3.0 |
| L-leucine | 2.9 |
| L-isoleucine | 2.2 |
| Fats | 8.9 |
| Vitamins and Minerals | 4.6 |
| Carbohydrates | 48.8 | the remaining ingredients comprising flavoring and emulsifiers.

3. An arginine supplemented dietary composition for enteral administration to human patients who have an impaired immune response due to accidental or surgical trauma, or who are suffering from a debilitating disease or due to old age, or due to severe malnourishment, the composition including the following ingredients in relative proportions:

| Ingredients | Grams |
|---|---|
| L-isoleucine | 3.5 |
| L-leucine | 6.1 |
| L-lysine | 1.8 |
| L-methionine | 0.5 |
| L-phenylalanine | 0.6 |
| L-tryptophan | 0.4 |
| L-threonine | 0.9 |
| L-valine | 4.5 |
| L-arginine | 7.5 |
| L-histidine | 0.3 |
| L-alanine | 1.0 |
| L-proline | 0.8 |
| Glycine | 0.4 |
| L-serine | 0.8 |
| L-tyrosine | 0.7 |
| L-glutamine | 4.5 |
| L-glutamic Acid | 3.3 |
| L-aspartic Acid | 2.1 |
| L-cysteine | 0.3 |
| Taurine | 0.1 |
| Maltodextrose | 60.0 |
| Fats | 11.0 |
| Vitamins and Minerals | 5.7 |

4. The arginine supplemented composition of claim 3 further comprising lactalbumin, wherein the lactalbumin provide a portion of the amino acids in said composition.

5. An arginine supplemented dietary composition for enteral administration to human patients who have an impaired immune response due to accidental or surgical trauma, who are suffering from a debilitating disease or due to old age, or who are severely malnourished, the composition including the following relative amounts of amino acid in grams:

| Amino Acids | Grams |
| --- | --- |
| L-isoleucine | 3.0–4.0 |
| L-leucine | 5.2–7.0 |
| L-lysine | 1.5–2.1 |
| L-methionine | 0.4–0.6 |
| L-phenylalanine | 0.5–0.7 |
| L-tryptophan | 0.3–0.7 |
| L-threonine | 0.8–1.0 |
| L-valine | 3.8–5.2 |
| L-arginine | 6.4–8.6 |
| L-histidine | 0.2–0.4 |
| L-alanine | 0.9–1.1 |
| L-proline | 0.7–0.9 |
| Glycine | 0.3–0.5 |
| L-serine | 0.7–0.9 |
| L-tyrosine | 0.6–0.8 |
| L-glutamine | 3.8–5.2 |
| L-glutamic Acid | 2.8–3.8 |
| L-aspartic Acid | 1.8–2.4 |
| L-cysteine | 0.2–0.4 |
| Taurine | 0.1–0.2 |

6. An arginine supplemented dietary composition for enteral administration to human patients who have an impaired immune response who have been subjected to or due to accidental or surgical trauma, who are suffering from a debilitating disease or due to old age, or due to severe malnourishment, the composition including the following amino acid concentrations in terms of % weight of individual amino acids to the total weight of the amino acids in the composition (% w/w):

| Amino Acids | % w/w |
| --- | --- |
| L-isoleucine | 8.6 |
| L-leucine | 15.2 |
| L-lysine | 4.6 |
| L-methionine | 1.2 |
| L-phenylalanine | 1.5 |
| L-tryptophan | 0.9 |
| L-threonine | 2.4 |
| L-valine | 11.2 |
| L-arginine | 18.7 |
| L-histidine | 0.7 |
| L-alanine | 2.6 |
| L-proline | 2.1 |
| Glycine | 0.9 |
| L-serine | 1.9 |
| L-tyrosine | 1.7 |
| L-glutamine | 11.2 |
| L-glutamic Acid | 8.4 |
| L-aspartic Acid | 5.3 |
| L-cysteine | 0.8 |
| Taurine | 0.3 |

7. An amino acid solution for parenteral administration to human patients who have an impaired immune response, who have been subjected to accidental or surgical trauma, or who are suffering from a debilitating disease or from old age, or who are severely malnourished, the solution incorporating essential and non-essential amino acids in the following ranges:

| Amino Acid | % w/w |
| --- | --- |
| Essentials | |
| L-isoleucine | 8.7 |
| L-leucine | 15.3 |
| L-lysine.Ac (Lys Eq) | 6.8 |
| L-methionine | 7.2 |
| L-phenylalanine | 4.2 |
| L-tryptophan | 2.9 |
| L-threonine | 4.8 |
| L-valine | 11.3 |
| L-arginine | 14.1 |
| L-histidine | 3.4 |
| Non-Essentials | |
| L-alanine | 3.9 |
| L-proline | 4.9 |
| Glycine | 1.2 |
| L-serine | 2.8 |
| L-tyrosine | 0.5 |
| N-acetyl-L-tyrosine (Tyr Eq) | 2.4 |
| L-glutamic Acid | 2.6 |
| L-aspartic Acid | 2.6 |
| L-cysteine.HCl.H20 | 0.2 |
| Taurine | 0.4 | wherein the % w/w can vary ±15% of the % w/w value for each amino acid.

8. A method for treating an impaired human immune response which comprises parenterally administering to a human with said impaired immune response, a therapeutically effective amount of arginine or ornithine, or a functional analog of arginine or ornithine, or mixtures thereof, in an amount greater than 15 grams per day up to an amount which continues to be therapeutically effective, said functional analog being a compound selected from the group consisting of salts of arginine or ornithine, peptides containing arginine or ornithine and derivatives of arginine and ornithine which retain the functional characteristics of arginine and ornithine in the treatment of said impaired immune response.

9. The method of claim 8 wherein the impaired immune response is substantially associated with trauma.

10. The method of claim 8 wherein the impaired immune response is substantially associated with major surgical procedures.

11. The method of claim 8 wherein the impaired immune response is substantially associated with malnutrition.

12. The method of claim 8 wherein the impaired immune response is substantially associated with cancer.

13. The method of claim 8 wherein the impaired immune response is substantially the result of HIV (AIDS) virus infections.

14. The method of claim 8 wherein the amount of arginine or ornithine, or a functional analog of arginine or ornithine, or mixtures thereof, administered to the human is such that the total amount of arginine or ornithine, or a functional analog of arginine or ornithine, or mixtures thereof, provided to the human is from about 15 grams to about 35 grams per day.

15. A method for treating an impaired human immune response which is impaired due to causes other than from infection with the HIV virus, the method which comprises parenterally administering to a human with an impaired immune response a sufficient quantity of arginine or ornithine, or a functional analog of arginine or ornithine, or mixtures thereof, as a supplement to the normal diet so that the total intake of arginine or ornithine, or a functional analog of arginine or ornithine, or mixtures thereof, is at least about 15 grams per day up to an amount which continues to be therapeutically effective, said functional analog being a compound selected from the group consisting of salts of arginine or ornithine, peptides containing arginine or ornithine and derivatives of arginine and ornithine which retain the functional characteristics of arginine and ornithine in the treatment of impaired immune response.

16. The method of claim 15 wherein the impaired immune response is substantially associated with trauma.

17. The method of claim 15 wherein the impaired immune response is substantially associated with major surgical procedures.

18. The method of claim 15 wherein the impaired immune response is substantially associated with malnutrition.

19. The method of claim 15 wherein the impaired immune response is substantially associated with cancer.

20. The method of claim 15 wherein the impaired immune response is substantially the result of HIV (AIDS) virus infections.

21. The method of claim 15 wherein the amount of the supplement is such that the total amount of arginine or ornithine, or a functional analog of arginine or ornithine, or mixtures thereof, provided to the immune-impaired human is from at least about 15 grams per day to about 35 grams per day.

22. A method for reducing the severity of degradation of immune response in a human who has suffered accidental or surgical trauma or a debilitating disease which comprises parenterally administering to a human who has suffered accidental or surgical trauma or a debilitating disease a therapeutically effective amount of arginine or ornithine, or a functional analog of arginine or ornithine, or mixtures thereof, in an amount greater than 15 grams per day up to an amount which continues to be therapeutically effective, said functional analog being a compound selected from the group consisting of salts of arginine or ornithine, peptides containing arginine or ornithine and derivatives of arginine and ornithine which retain the functional characteristics of arginine and ornithine in the treatment of impaired immune response.

23. The method of claim 22 wherein the amount of arginine or ornithine, or a functional analog of arginine or ornithine, or mixtures thereof, administered is such that the total amount of arginine or ornithine, or a functional analog of arginine or ornithine, or mixtures thereof, provided to the human is from about 15 grams to about 35 grams per day.

24. A method for reducing the severity of degradation of immune response in a human who has suffered accidental or surgical trauma or a debilitating disease which comprises parenterally administering to a human who has suffered accidental or surgical trauma or a debilitating disease a sufficient amount of arginine or ornithine, or a functional analog of arginine or ornithine, or mixtures thereof, as a supplement to the normal diet so that the total intake of arginine or ornithine, or a functional analog of arginine or ornithine, or mixtures thereof, is at least about 15 grams per day up to an amount which continues to be therapeutically effective, said functional analog being a compound selected from the group consisting of salts of arginine or ornithine, peptides containing arginine or ornithine and derivatives of arginine and ornithine which retain the functional characteristics of arginine and ornithine in the treatment of impaired immune response.

25. The method of claim 24 wherein the amount of arginine or ornithine, or a functional analog of arginine or ornithine, or mixtures thereof, administered to the human is such that the total amount of arginine or ornithine, or a functional analog of arginine or ornithine, or mixtures thereof, provided to the human is from about 15 grams to about 35 grams per day.

26. A method for treating a human patient who tests seropositive for HIV (AIDS) virus infection, the method comprising administering to the patient arginine or ornithine, or a functional analog or arginine or ornithine, or mixtures thereof, in an amount greater than 15 grams per day up to an amount which continues to be therapeutically effective, said functional analog being a compound selected from the group consisting of salts of arginine or ornithine, peptides containing arginine or ornithine and derivatives of arginine and ornithine which retain the functional characteristics of arginine and ornithine in the treatment of impaired immune response.

27. The method of claim 26 wherein the amount of arginine or ornithine, or a functional analog of arginine or ornithine, or mixtures thereof, administered to the patient is such that the total amount of arginine or ornithine, or a functional analog of arginine or ornithine, or mixtures thereof, consumed by the patient is from 15 grams per day to 35 grams per day.

28. The method of claim 27 wherein the arginine or ornithine, or functional analog of arginine or ornithine, or mixtures thereof, is provided by parenteral administration.

29. A method for treating an impaired human immune response, the method comprising enterally administering to a human with an impaired immune response a composition comprising arginine or ornithine, or a functional analog of arginine or ornithine, or mixtures thereof, and L-isoleucine, L-leucine, L-lysine, L-methionine, L-phenylalanine, L-tryptophan, L-threonine, L-valine and L-histidine, wherein said administration results in the total amount of arginine or ornithine, or a functional analog of arginine or ornithine, or mixtures thereof, administered to the patient per day of at least 15 grams up to an amount which continues to be therapeutically effective, said functional analog being a compound selected from the group consisting of salts of arginine or ornithine, peptides containing arginine or ornithine and derivatives of arginine and ornithine which retain the functional characteristics of arginine and ornithine in the treatment of impaired immune response, wherein the following amounts of L-methionine, L-phenylalanine, L-tryptophan, L-threonine, L-valine and L-histidine are administered each day to the patient:

| Amino Acids | Grams/Day |
| --- | --- |
| L-isoleucine | 12.0–16.0 |
| L-leucine | 20.8–28.0 |
| L-lysine | 6.0–8.4 |
| L-methionine | 1.6–2.4 |
| L-phenylalanine | 2.0–3.0 |
| L-tryptophan | 1.2–2.0 |
| L-threonine | 3.2–4.0 |
| L-valine | 15.2–21.0 |
| L-histidine | 0.8–1.6 |

30. The method of claim 29 wherein the total amount of arginine or ornithine, or a functional analog of arginine or ornithine, or mixtures thereof, administered to the patient is from 15 to about 35 grams per day.

31. The method of claim 29 wherein 15 to 35 grams of arginine are administered per day to the patient.

32. The method of claim 29 wherein the impaired immune response is substantially associated with trauma.

33. The method of claim 29 wherein the impaired immune response is substantially associated with major surgical procedures.

34. The method of claim 29 wherein the impaired immune response is substantially associated with malnutrition.

35. The method of claim 29 wherein the impaired immune response is substantially associated with cancer.

36. The method of claim 29 wherein the impaired immune response is substantially the result of HIV (AIDS) virus infections.

37. The method of claim 29 wherein the composition additionally comprises the non-essential amino acids alanine, proline, glycine, serine, tyrosine, glutamic acid, aspartic acid, cysteine, and taurine.

38. The method of claim 37 wherein the following total amounts of the amino acids set forth in the claim 34 are administered each day to the patient:

| Amino Acids | Grams/Day |
| --- | --- |
| L-alanine | 3.6–4.4 |
| L-proline | 2.8–3.6 |
| Glycine | 1.2–2.0 |
| L-serine | 2.8–3.6 |
| L-tyrosine | 2.4–3.2 |
| L-glutamine | 15.2–20.8 |
| L-glutamic Acid | 11.2–15.2 |
| L-aspartic Acid | 7.2–9.6 |
| L-cysteine | 0.8–1.6 |
| Taurine | 0.4–0.8 |

* * * * *

UNITED STATES PATENT AND TRADEMARK OFFICE
CERTIFICATE OF CORRECTION

PATENT NO. : 5,576,351
DATED : November 19, 1996
INVENTOR(S) : Norman N. Yoshimura; Adrian Burbul; Robert C. Tao; Michael C. Storm; Robert E. Kelley; Brenda L. Reis It is certified that error appears in the above-indentified patent and that said Letters Patent is hereby corrected as shown below:

On the title page:

Item [56], References Cited, U.S. PATENT DOCUMENTS,
        change "5,231,085  4/1993  Alexander et al...514/44"
        to -- 5,231,085  7/1993  Alexander et al...514/44 --.
Other Publications, page 2, column 2, line 42, in the publication of
        "Barbul et al." change "19900." to -- (1990). --.
Column 1, lines 9,10, replace "Dec. 12, 1990" with -- Dec. 28, 1990 --.
Column 4, line 58, change "responses" to -- response --.
Column 8, line 56, change "acids" to -- acid --.
Column 12, line 36, delete the sentence "When prepared from desirably free of ammonia.".
Column 12, line 57, change "parental" to -- parenteral --.
Column 13, lines 32, 36, 37, change "ul" to -- µl -- (all occurrences).
Column 13, line 53, change "ul" to -- µl --.
Column 15, line 5, change "ug" to -- µl --.
Column 15, lines 20,24, 27, 29, 34, change "ul" to -- µl -- (all occurrences).
Column 1, line 9, delete --division--.

UNITED STATES PATENT AND TRADEMARK OFFICE
CERTIFICATE OF CORRECTION

PATENT NO. : 5,576,351
DATED : November 19, 1996
INVENTOR(S) : Norman N. Yoshimura; Adrian Burbul; Robert C. Tao; Michael C. Storm; Robert E. Kelley; Brenda L. Reis It is certified that error appears in the above-indentified patent and that said Letters Patent is hereby corrected as shown below:

Column 19, line 7, Table 14, in the heading, second column, replace "Supple*" with -- Suppl.* --.

Column 20, line 39, replace "slowing added" with -- slowly adding --.

Column 20, line 41, change "1 minutes" to -- 1 minute --.

Column 23, line 1, claim 5, change "response due" to -- response, who have been subjected --.

Column 23, lines 2-3, claim 5, replace "or due to old age" with -- or from old age --.

Column 23, lines 30-31, claim 6, replace "response who have been subjected to or due to" with -- response, who have been subjected to --.

Column 23, lines 32-33, claim 6, replace "or due to old age, or due to severe malnourishment" with -- or old age, or who are severely malnourished --.

Column 24, lines 59-60, claim 15, delete "which is impaired due to causes other than from infection with the HIV virus, the method".

UNITED STATES PATENT AND TRADEMARK OFFICE
CERTIFICATE OF CORRECTION

PATENT NO. : 5,576,351
DATED : November 19, 1996
INVENTOR(S) : Norman N. Yoshimura; Adrian Burbul; Robert C. Tao; Michael C. Storm; Robert E. Kelley; Brenda L. Reis It is certified that error appears in the above-indentified patent and that said Letters Patent is hereby corrected as shown below:

Column 26, line 6, claim 26, after "analog" change "or" to -- of --.
Column 26, line 45, claim 29, after "amounts of" insert -- L-isoleucine, L-leucine, L-lysine --.
Column 27, line 16, claim 37, after "glutamic acid," insert -- glutamine, --.
Column 28, line 2, claim 38, replace "acids set forth in the claim 34" with -- acids in addition to those set forth in the claim 29 --.

Signed and Sealed this

Thirtieth Day of December, 1997

*Attest:*

BRUCE LEHMAN

*Attesting Officer*  *Commissioner of Patents and Trademarks*